United States Patent
Butts et al.

(10) Patent No.: US 9,399,075 B2
(45) Date of Patent: *Jul. 26, 2016

(54) NANOPARTICLE CONTRAST AGENTS FOR DIAGNOSTIC IMAGING

(71) Applicant: General Electric Company, Schenectady, NY (US)

(72) Inventors: Matthew David Butts, Rexford, NY (US); Robert Edgar Colborn, Niskayuna, NY (US); Peter John Bonitatibus, Jr., Saratoga Springs, NY (US); Andrew Soliz Torres, Troy, NY (US); Brian Christopher Bales, Niskayuna, NY (US); Michael Ernest Marino, Clifton Park, NY (US); Bruce Allan Hay, Niskayuna, NY (US); Amit Mohan Kulkarni, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 498 days.

This patent is subject to a terminal disclaimer.

(21) Appl. No.: 13/872,539

(22) Filed: Apr. 29, 2013

(65) Prior Publication Data

US 2014/0147387 A1    May 29, 2014

Related U.S. Application Data

(63) Continuation-in-part of application No. 12/344,606, filed on Dec. 29, 2008, now Pat. No. 8,728,529, and a continuation-in-part of application No. 13/592,853, filed on Aug. 23, 2012, now Pat. No. 8,728,440.

(51) Int. Cl.
 *A61K 49/04* (2006.01)
 *C01G 35/00* (2006.01)
 (Continued)

(52) U.S. Cl.
 CPC ......... *A61K 49/0002* (2013.01); *A61K 49/0428* (2013.01); *A61K 49/1848* (2013.01);
 (Continued)

(58) Field of Classification Search
 None
 See application file for complete search history.

(56) References Cited

U.S. PATENT DOCUMENTS 6,207,134 B1   3/2001   Fahlvik et al.
6,391,818 B1   5/2002   Bonsel et al.
(Continued)

FOREIGN PATENT DOCUMENTS

DE      19754304 A1    6/1999
DE      10106643 A1   11/2001
(Continued)

OTHER PUBLICATIONS

M Ma, Y Zhang, W Yu, H-Y Shen, H-Q Zhang, N Gu. "Preparation and characterization of magnetite nanoparticles coated by amino silane." Colloids and Surfaces A: Physiochemical and Engineering Aspects, vol. 212, 2003, pp. 219-226.*
(Continued)

*Primary Examiner* — Isaac Shomer
(74) *Attorney, Agent, or Firm* — Paul J. DiConza

(57) ABSTRACT

Compositions of nanoparticles functionalized with at least one zwitterionic moiety, methods for making a plurality of nanoparticles, and methods of their use as diagnostic agents are provided. The nanoparticles have characteristics that result in minimal retention of the particles in the body compared to other nanoparticles. The nanoparticle comprising a nanoparticulate transition metal oxide covalently functionalized with a silane-functionalized non-targeting zwitterionic moiety.

11 Claims, 6 Drawing Sheets

Figure 1:
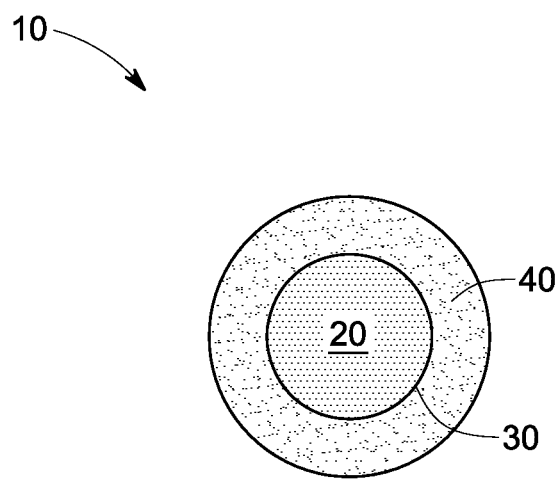

(51) Int. Cl.
| | |
|---|---|
| A61K 49/00 | (2006.01) |
| A61K 49/18 | (2006.01) |
| B82Y 5/00 | (2011.01) |
| B82Y 30/00 | (2011.01) |

(52) U.S. Cl.
CPC . B82Y 5/00 (2013.01); B82Y 30/00 (2013.01); *C01G 35/00* (2013.01); *Y10S 977/779* (2013.01); *Y10S 977/927* (2013.01); *Y10S 977/928* (2013.01); *Y10T 428/2982* (2015.01)

(56) References Cited

U.S. PATENT DOCUMENTS

| | | | |
|---|---|---|---|
| 6,410,765 | B1 | 6/2002 | Wellinghoff et al. |
| 7,138,468 | B2 | 11/2006 | Mccormick, III et al. |
| 7,598,335 | B2 | 10/2009 | Wang et al. |
| 8,574,549 | B2 * | 11/2013 | Butts et al. .................. 424/9.32 |
| 8,728,440 | B2 * | 5/2014 | Butts ..................... C07F 7/1836 424/489 |
| 8,728,529 | B2 * | 5/2014 | Butts et al. ..................... 424/489 |
| 8,821,838 | B2 * | 9/2014 | Bonitatibus et al. ......... 424/9.42 |
| 2003/0059472 | A1 | 3/2003 | Brynjelsen et al. |
| 2004/0105980 | A1 | 6/2004 | Sudarshan et al. |
| 2006/0216239 | A1 | 9/2006 | Zhang et al. |
| 2007/0068343 | A1 | 3/2007 | Lukehart et al. |
| 2007/0082190 | A1 | 4/2007 | Endres et al. |
| 2007/0098640 | A1 | 5/2007 | Bonitatebus et al. |
| 2007/0098641 | A1 | 5/2007 | Bonitatebus et al. |
| 2007/0098642 | A1 | 5/2007 | Bonitatebus et al. |
| 2007/0122620 | A1 * | 5/2007 | Bonitatebus et al. ......... 428/403 |
| 2007/0140974 | A1 * | 6/2007 | Torres et al. ............... 424/9.323 |
| 2008/0089836 | A1 | 4/2008 | Hainfeld |
| 2008/0095699 | A1 | 4/2008 | Zheng et al. |
| 2009/0238767 | A1 | 9/2009 | Hummel et al. |
| 2010/0119458 | A1 | 5/2010 | Uvdal |

FOREIGN PATENT DOCUMENTS

| | | |
|---|---|---|
| JP | 2008524202 A1 | 7/2008 |
| WO | 0178689 A2 | 10/2001 |
| WO | 02060998 A2 | 8/2002 |
| WO | 03002225 A1 | 1/2003 |
| WO | 03075961 A2 | 9/2003 |
| WO | 2005070979 A1 | 8/2005 |
| WO | 2007021946 A2 | 2/2007 |
| WO | 2007055995 A2 | 5/2007 |
| WO | 2007069040 A2 | 6/2007 |
| WO | 2007146680 A1 | 12/2007 |
| WO | WO 2007146680 A1 * | 12/2007 |
| WO | 2009047587 A1 | 4/2009 |

OTHER PUBLICATIONS

CAS Registry Record for CAS# 1233477-94-5. Entered STN Jul. 22, 2010, 1 printed page.*
CAS Registry Record for CAS# 1233478-02-8. Entered STN Jul. 22, 2010, 1 printed page.*
CAS Registry Record for CAS# 1233478-03-9. Entered STN Jul. 22, 2010, 1 printed page.*
JF Satchell, BJ Smith. "Calculation of aqueous dissociation constants of 1,2,4-triazole and tetrazole: A comparison of solvation models." Physical Chemistry Chemical Physics, vol. 4, 2002, pp. 4314-4318.*
Salkar et al., "Elongated Copper Nanoparticles Coated with a Zwitterionic Surfactant", J. Phys. Chem. B, vol. 104(5), pp. 893-897, 2000.
Fu et al., "Self-Assembled (SA) Bilyaer Molecular Coating on Magnetic Nanoparticles", Applied Surface Science, vol. 181, pp. 173-178, 2001.
McCormick et al., "Aqueous RAFT Polymerization: Recent Developments in Synthesis of Functional Water-Soluble (Co)polymers with Controlled Structures", Accounts of Chemical Research, vol. 37, No. 5, pp. 312-325, 2004.

Tatumi et al., "Remarkably stable gold nanoparticles functionalized with a zwitterionic liquid based on imidazolium sulfonate in a high concentration of aqueous electrolyte and ionic liquid", The Royal Society of Chemistry, pp. 83-85, 2005.
Kitadai et al., "Synthesis, structures and reactions of cyclometallated gold complexes containing (2-diphenylarsino-n-methyl)phenyl (n=5, 6)", The Royal Society of Chemistry, pp. 2560-2571, 2006.
Starck et al., "Surface Chemistry and Rheology of Polysulfobetaine-Coated Silica", Langmuir, vol. 23(14), pp. 7587-7593, 2007.
Rouhana et al., "Aggregation-Resistant Water-Soluble Gold Nanoparticles", Department of Chemistry and Biochemistry, Center for Materials Research and Technology (MARTECH), The Florida State UniVersity, Tallahassee, Florida, Langmuir, vol. 23, pp. 12799-12801, 2007.
Choi et al., "Renal clearance of quantum dots", Nature Biotechnology, vol. 25, Issue No. 10, pp. 1165-1170, Oct. 2007.
Ding et al., "Reversible Assembly and Disassembly of Gold Nanoparticles Directed by a Zwitterionic Polymer", Chem. Eur. J., vol. 13, pp. 4197-4202, 2007.
Jin et al., "Zwitterionic phosphorylcholine as a better ligand for stabilizing large biocompatible gold nanoparticles", The Royal Society of Chemistry, Chem. Commun., pp. 3058-3060, 2008.
Markowitz et al., "Polymerized Phospholipid Membrane Mediated Synthesis of Metal Nanoparticles", Langmuir, vol. No. 10, Issue No. 11, pp. 4095-4102, 1994.
Markowitz et al., "Phospholipid Membranes as Templates for Synthesis of Gold Nanoparticles", Proceedings of the American Chemical Society Division of Polymeric Materials: Science and Engineering, vol. No. 73, p. 260, Chicago, Illinois, USA, Aug. 20-24, 1995.
Butun et al., "Synthesis of Zwitterionic Shell Cross-Linked Micelles", Journal of the American Chemical Society, vol. No. 121, Issue No. 17, pp. 4288-4289, 1999.
Ma et al., "Nanoscopic, Zwitterionic Domains Incorporated Across the Surface of Shell-Crosslinked Nanoparticles", 222nd ACS National Meeting, PMSE-324, Chicago, IL, USA, Aug. 26-30, 2001.
Ma et al., "Nanoscopic, Zwitterionic Domains Incorporated Across the Surface of Shell-Crosslinked (SCK) Nanoparticles", Polymeric Materials Science and Engineering, vol. 85, p. 543, Aug. 26-30, 2001.
Ma et al., "Preparation and Characterization of Magetite Nanoparticle Coated by Amino Sillane", Colliods and Surfaces A: Physicochem. Eng. Aspects 212, 219-226, 2003.
Ipe, et al., "Light-Induced Modulation of Self-Assembly on Spiropyran-Capped Gold Nanoparticles: A Potential System for the Controlled Release of Amino Acid Derivatives", Journal of the American Chemical Society, vol. No. 125, Issue No. 24, pp. 7174-7175, 2003.
Sameti et al., "Stabilisation by Freeze-Drying of Cationically Modified Silica Nanoparticles for Gene Delivery", International Journal of Pharmaceutics, vol. No. 266, Issue No. 1-2, pp. 51-60, 2003.
Tiyapiboonchaiya et al., "The Zwitterion Effect in High-Conductivity Polyelectrolyte Materials", Nature Materials, vol. No. 03, Issue No. 01, pp. 29-32, 2004.
Ghosh et al., "Solvent and Ligand Effects on the Localized Surface Plasmon Resonance (LSPR) of Gold Colloids", Journal Physics and Chemistry B, vol. No. 108, Issue No. 37, pp. 13963-13971, 2004.
Kitano et al., "Resistance of Zwitterionic Telomers Accumulated on Metal Surfaces Against Nonspecific Adsorption of Proteins", Journal of Colloid and Interface Science, vol. No. 282, Issue No. 2, pp. 340-348, Feb. 15, 2005.
Byrne et al., "Composition Effects on Ion Transport in a Polyelectrolyte Gel with the Addition of Ion Dissociators", Electrochimica Acta, vol. No. 50, Issue No. 19, pp. 3917-3921, Jun. 30, 2005.
Al-Kaysi et al., "Effects of Sonication on the Size and Crystallinity of Stable Zwitterionic Organic Nanoparticles Formed by Reprecipitation in Water", Langmuir, vol. No. 21, Issue No. 17, pp. 7990-7994, 2005.
Singh et al., "Surface Modification of Adenovirus by Zwitterionic (DMPC-Chol) Liposomes can Up- or Down-Regulated Adenoviral Gene Transfer Efficiency in Vitro", Journal of Drug Delivery Science and Technology, vol. No. 15, Issue No. 4, pp. 289-294, 2005.

(56) References Cited

OTHER PUBLICATIONS

Nath et al., "Silver Organosol: Synthesis, characterization and localized surface plasmon resonance study", New Journal of Chemistry, vol. No. 29, Issue No. 12, pp. 1527-1534, 2005.

Singh et al., "Synthesis of Gold, Silver and their Alloy Nanoparticles using Bovine Serum Albumin as Foaming and Stabilizing Agent", Journal of Materials Chemistry, vol. No. 15, Issue No. 48, pp. 5115-5121, 2005.

Rouhana et al., "Synthesis of Aggregation-Resistant Gold Nanoparticles", 231st ACS National Meeting, Atlanta, COLL-250, Atlanta, GA, United States, Mar. 26-30, 2006.

Singh et al., "Engineering artificial envelopes for non-enveloped viral nanoparticles", 232nd ACS National Meeting, COLL-168, San Francisco, CA, United States, Sep. 10-14, 2006.

Ju-Nam et al., "Phosphonioalkylthiosulfate Zwitterions—New Masked Thiol Ligands for the Formation of Cationic Functionalised Gold Nanoparticles", Org Biomol Chem., vol. No. 4, Issue No. 23, pp. 4345-4351, Dec. 2006.

Lim et al., "Homocysteine-Mediated Reactivity and Assembly of Gold Nanoparticles", Langmuir, vol. No. 23, Issue No. 2, pp. 826-833, 2007.

Rouhana et al., "Synthesis of Stable, Water Soluble Gold Nanoclusters", American Chemical Society, COLL-085, Washington, D. C, USA, Mar. 25-29, 2007.

Matsuura et al., "Carboxybetaine Polymer-Protected Gold Nanoparticles: High Dispersion Stability and Resistance against Non-Specific Adsorption of Proteins", Macromolecular Chemistry and Physics, vol. No. 208, Issue No. 8, pp. 862-873, Apr. 2007.

Yu et al., "Cationic Nanoparticles Stabilize Zwitterionic Liposomes Better than Anionic Ones", J. Phys. Chem. C, vol. No. 111, Issue No. 23, pp. 8233-8236, 2007.

Mitric et al., "Photoabsorption and Photofragmentation of Isolated Cationic Silver Cluster-Tryptophan Hybrid Systems", J Chem Phys., vol. No. 127, Issue No. 13, pp. 134301/1-134301/9, Oct. 2007.

Horovitz et al., "Lysine Mediated Assembly of Gold Nanoparticles", Studia Universitatis Babeş-Bolyai, Chemia, vol. No. 52, Issue No. 1, pp. 97-108, 2007.

Irvine "Applying Nanomaterials to Immunology", PMSE Preprints, vol. No. 99, p. 684, Pennsylvania, USA, Aug. 21-28, 2008.

Daisuke "3-Isocyanatepropyltrimethoxysilane", Chemical Book, Jan. 21, 2014 (Unofficial English Translation).

Unofficial English Translation of Japanese Office Action issued from JP Application No. 2011542782 on Jan. 21, 2014.

Unofficial English Translation of Japanese Office Action issued from JP Application No. 2011542782 on Feb. 3, 2015.

* cited by examiner

Organic Acids

Carboxylic acids phosphonic acids

N-acylsulfonamides sulfonic acids monoalkylphosphonates imides sulfinic acids monoalkylphosphates tetrazoles Malonate derivatives dialkylphosphates aryl alcohols Organic Bases 1°, 2°, 3°, 4° amines amidines guanidines pyridines pyrimidines pyrazines imidazoles pyrroles purines N,N-dimethyl-3-sulfo-N-(3-
(trimethoxysilyl)propyl)propan-1-aminium 3-(methyl(3-(trimethoxysilyl)propyl)amino)propane-1-
sulfonic acid 3-(3-(trimethoxysilyl)propylamino)propane-1-sulfonic acid 2-(2-(trimethylsilyl)ethoxy(hydroxy)phosphoryloxy)-
N,N,N-trimethylethanaminium 2-(2-(trimethoxysilyl)ethyl(hydroxy)phosphoryloxy)-
N,N,N-trimethylethanaminium N,N,N-trimethyl-3-(N-3-(trimethoxysilyl)propionyl-
sulfamoyl)propan-1-aminium N-((2H-tetrazol-5-yl)methyl)-N,N-dimethyl-3-
(trimethoxysilyl)propan-1-aminium N-(2-carboxyethyl)-N,N-dimethyl-3-
(trimethoxysilyl)propan-1-aminium 3-(methyl(3-(trimethoxysilyl)propyl)amino)propanoic acid 3-(3-(trimethoxysilyl)propylamino)propanoic acid N-(carboxymethyl)-N,N-dimethyl-3-
(trimethoxysilyl)propan-1-aminium 2-(methyl(3-(trimethoxysilyl)propyl)amino)acetic acid 2-(3-(trimethoxysilyl)propylamino)acetic acid 2-(4-(3-(trimethoxysilyl)propylcarbamoyl)piperazin-1-yl)acetic acid 3-(4-(3-(trimethoxysilyl)propylcarbamoyl)piperazin-1-yl)propanoic acid 2-(methyl(2-(3-(trimethoxysilyl)propylureido)ethyl)amino)acetic acid 2-(2-(3-(trimethoxysilyl)propylureido)ethyl)aminoacetic acid N-(2-tertiary butyl acetate)-N-N-dimethyl-3-(trimethoxysilyl) propane-1-aminium

NANOPARTICLE CONTRAST AGENTS FOR DIAGNOSTIC IMAGING

CROSS REFERENCE TO RELATED APPLICATIONS

This application is a continuation-in-part of U.S. patent application Ser. No. 12/344,606, entitled "NANOPARTICLE CONTRAST AGENTS FOR DIAGNOSTIC IMAGING", filed on Dec. 29, 2008, which is herein incorporated by reference and is a continuation-in-part of U.S. patent application Ser. No. 13/592,853, entitled "NANOPARTICULATE COMPOSITIONS FOR DIAGNOSTIC IMAGING", filed on Aug. 23, 2012, which is herein incorporated by reference.

BACKGROUND

This application relates generally to contrast agents for diagnostic imaging, such as for use in X-ray/Computed Tomography (CT) or Magnetic Resonance Imaging (MRI). More particularly, the application relates to nanoparticle-based contrast agents, and methods for making and using such agents.

Iodinated aromatic compounds serve as standard X-ray/computed tomography (CT) contrast agents. Similarly, gadolinium chelates are the most commonly used contrast agents for Magnetic Resonance Imaging. Such standard contrast agents are typically of low molecular weight, and they are known to have disadvantages such as rapid clearance, leakage through blood vessel walls, lower sensitivity, high viscosity, high osmolality and toxicity. In the case of contrast agents, it is preferred to have maximum renal clearance of the agents from the body without causing short term or long term toxicity to any organs. Thus there is a need for a new class of contrast agents.

Nanoparticles are being widely studied for uses in medical applications, both diagnostic and therapeutic. While only a few nanoparticle-based agents are clinically approved for magnetic resonance imaging applications and for drug delivery applications, hundreds of such agents are still in development. There is substantial evidence that nanoparticles have benefits over currently used standard contrast agents in terms of efficacy for diagnostics and therapeutics. However, the effects of particle size, structure, and surface properties on the in-vivo bio-distribution and clearance of nanoparticle agents are not well understood.

In view of the above, there is a need for nanoparticle-based contrast agents with improved properties having high renal clearance and low toxicity.

BRIEF DESCRIPTION OF THE INVENTION

The present invention is directed to nanoparticle compositions, their method of making and methods of use.

The present invention provides a new class of nanoparticle-based contrast agents for X-ray, CT and MRI which are functionalized with non-targeting zwitterionic moieties. They have characteristics that result in minimal retention of the particles in the body compared to other nanoparticles. These nanoparticles may provide improved performance and benefit in one or more of the following areas: robust synthesis, reduced cost, image contrast enhancement, increased blood half life, and decreased toxicity.

One aspect of the invention relates to a composition comprising a nanoparticle. The nanoparticle comprises a nanoparticulate transition metal oxide covalently functionalized with a silane-functionalized non-targeting zwitterionic moiety. In some embodiments, the composition comprising a nanoparticle has an idealized structure I;

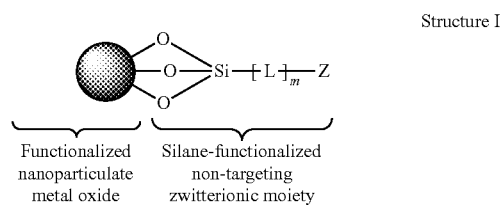

Structure I wherein, L is a linker, Z is the non-targeting zwitterionic moiety and m≥1. The nanoparticle is useful as diagnostic agent in medical imaging.

The nanoparticulate transition metal oxide may be selected from a group consisting of tungsten oxide, tantalum oxide, hafnium oxide, zirconium oxide, molybdenum oxide, bismuth oxide, silver oxide, zinc oxide, iron oxide, manganese oxide, copper oxide, cobalt oxide, nickel oxide, and combinations thereof.

In some embodiments, a composition comprises a nanoparticle. The nanoparticle comprises a nanoparticulate tantalum oxide covalently functionalized with a silane-functionalized non-targeting zwitterionic moiety. The nanoparticle may have an average particle size up to about 10 nm. In other embodiments, the nanoparticle comprises a nanoparticulate superparamagnetic iron oxide covalently functionalized with a silane-functionalized non-targeting zwitterionic moiety. The nanoparticle may have an average particle size up to about 50 nm.

In some embodiments, a composition comprises a nanoparticle which comprises a nanoparticulate tantalum oxide covalently functionalized with N,N-dimethyl-3-sulpho-N-(3-(trimethoxysilyl)propyl)propane-1-aminium. In one of the embodiments, the nanoparticle has an idealized structure II;

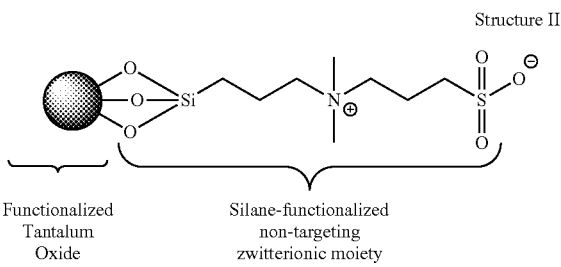 [SMILES: CO[Si](CCC[N+](C)(C)CCCS(=O)(=O)[O-])(OC)OC]

Structure II

In some embodiments, the composition comprises a nanoparticle comprising a nanoparticulate tantalum oxide covalently functionalized with 2-(4-(3-(trimethoxysilyl)propylcarbamoyl)piperazine-1-yl)acetic acid. In one of the embodiments, the nanoparticle has an idealized structure III;

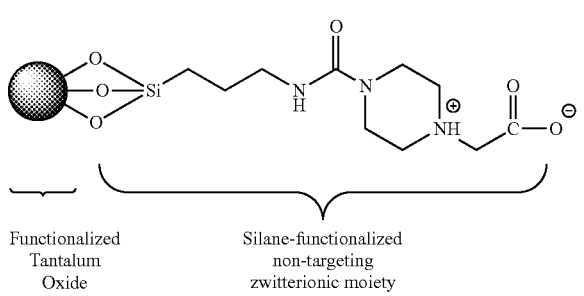

Structure III

Functionalized Tantalum Oxide — Silane-functionalized non-targeting zwitterionic moiety In other embodiments, the composition comprises a nanoparticle comprising a nanoparticulate tantalum oxide covalently functionalized with a trioxysilane betaine ligand. In one embodiment, the nanoparticle has an idealized structure IV;

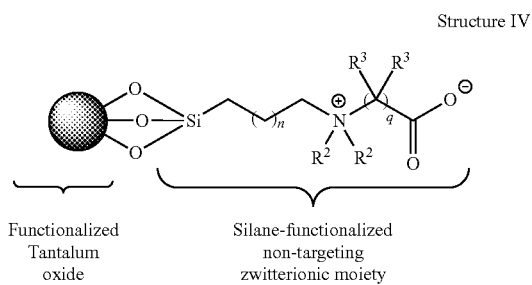

Structure IV

Functionalized Tantalum oxide — Silane-functionalized non-targeting zwitterionic moiety wherein $R^2$ is independently at each occurrence a $C_1$-$C_3$ alkyl group; $R^3$ is independently at each occurrence a hydrogen or a $C_1$-$C_3$ alkyl group; n is 0, 1, 2 or 3; q is 1, 2 or 3.

DRAWINGS

These and other features, aspects, and advantages of the present invention will become better understood when the following detailed description is read with reference to the accompanying drawings in which like characters represent like parts throughout the drawings, wherein:

FIG. 1 depicts a schematic view of a nanoparticle comprising a core and a shell, in accordance with some embodiments of the present invention.

Figure 2:
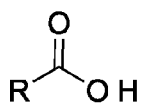
Figure 2:
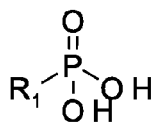
Figure 2:
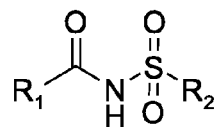
Figure 2:
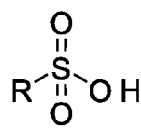
Figure 2:
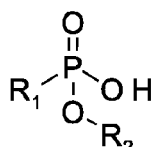
Figure 2:
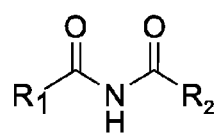
Figure 2:
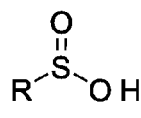
Figure 2:
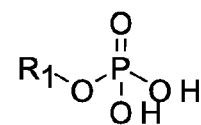
Figure 2:
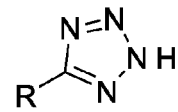
Figure 2:
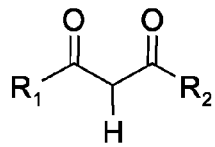
Figure 2:
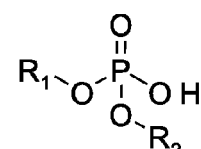
Figure 2:
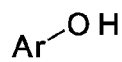
Figure 2:
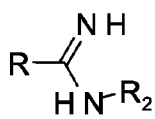
Figure 2:
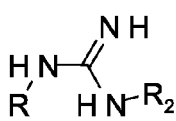
Figure 2:
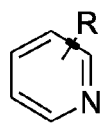
Figure 2:
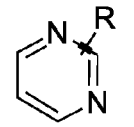
Figure 2:
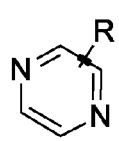
Figure 2:
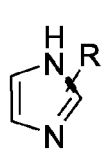
Figure 2:
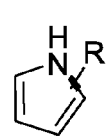
Figure 2:
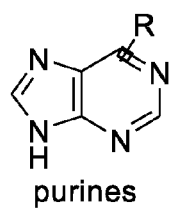
Figure 3A:
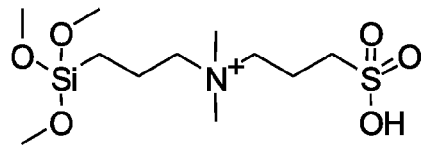
Figure 3A:
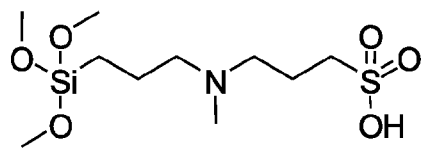
Figure 3A:
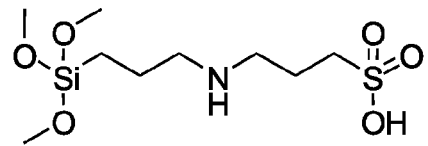
Figure 3A:
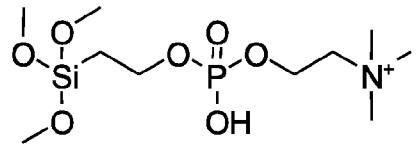
Figure 3A:
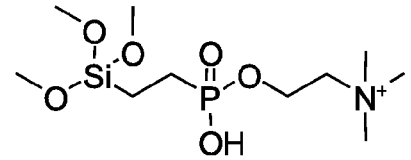
Figure 3B:
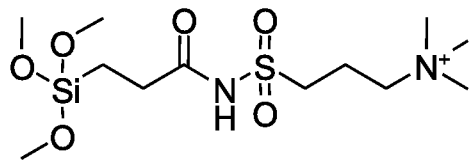
Figure 3B:
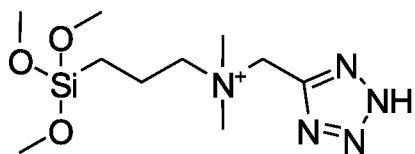
Figure 3B:
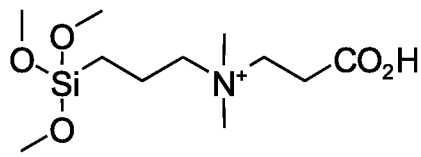
Figure 3B:
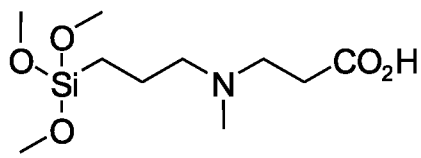
Figure 3C:
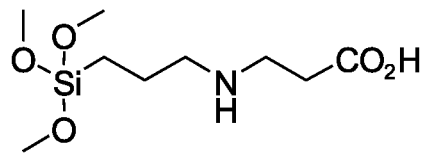
Figure 3C:
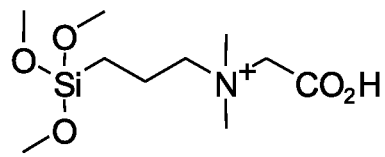
Figure 3C:
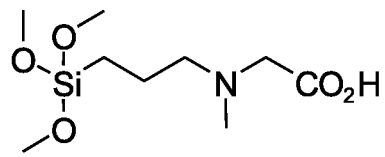
Figure 3C:
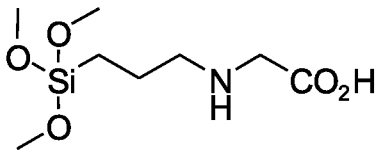
Figure 3D:
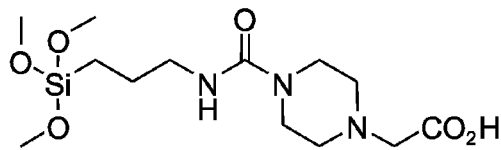
Figure 3D:
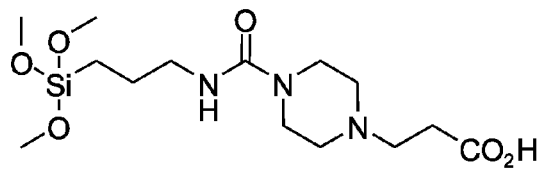
Figure 3D:
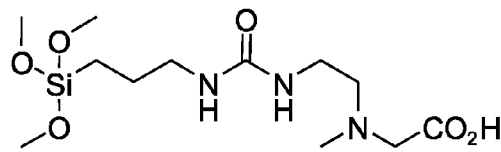
Figure 3D:
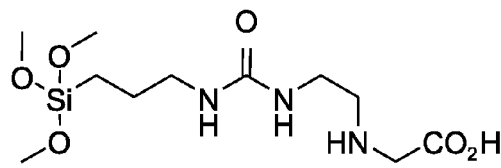
Figure 3D:
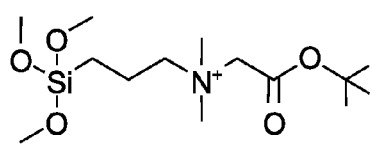

FIG. 2 describes organic acids and organic bases from which the zwitterionic functional moieties may be formed.

FIGS. 3A, 3B, 3C and 3D describe silane-functionalized zwitterionic moieties, which may be reacted with the nanoparticulate transition metal oxide to form a nanoparticle.

DETAILED DESCRIPTION

The following detailed description is exemplary and is not intended to limit the invention of the application or the uses of the invention. Furthermore, there is no intention to be limited by any theory presented in the preceding background of the invention or the following detailed description.

In the following specification and the claims which follow, the singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value.

As used herein, the term "Particle size" refers to hydrodynamic radius of the particle characterized by Dynamic Light Scattering.

As used herein, the term "Nanoparticle" refers to particles having a particle size on the nanometer scale, less than 1 micrometer. For example, the nanoparticle may have a particle size up to about 50 nm. In another example, the nanoparticle may have a particle size up to about 10 nm. In another example, the nanoparticle may have a particle size up to about 6 nm.

A transition metal oxide having size in nanometer range is referred as "Nanoparticulate transition metal oxide" since they can form the nanoparticle of the present composition upon functionalization.

As used herein, the term "Functionalized nanoparticulate transition metal oxide" refers to a transition metal oxide having a size in the nanometer range which is functionalized upon chemical reaction with the silane-functionalized non-targeting zwitterionic moiety. The term "functionalized" as used herein refers to "coated" or "partially coated" nanoparticulate transition metal oxide and wherein at least one silane functionalized non-targeting zwitterionic moiety is covalently bound via one or more oxygen-silicon bonds to the nanoparticulate metal oxide.

As used herein, the term "Silane-functionalized non-targeting zwitterionic moiety" refers to a structure comprising a silane moiety and a non-targeting zwitterionic moiety as shown in structure V. The silane moiety is coupled to the non-targeting zwitterionic moiety via a linker.

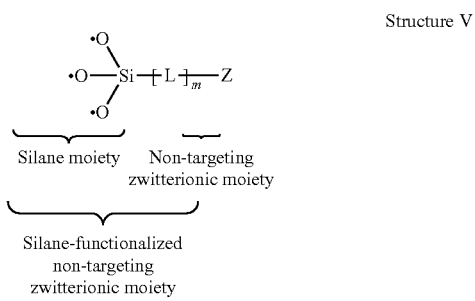

Structure V

Silane moiety — Non-targeting zwitterionic moiety

Silane-functionalized non-targeting zwitterionic moiety

In structure V, L is a linker, Z is a non-targeting zwitterionic moiety and m≥1. The non-targeting zwitterionic moiety is connected to the silicon atom of the silane moiety via a linker.

As used herein, the term "non-targeting zwitterionic moiety" refers to a zwitterionic moiety that does not actively target to a specific receptor or antigenic site in the cells of body tissue. In other words, the zwitterionic moiety does not act like an antibody or other type of ligand that seeks out and binds to a specific site of a tissue or body.

As used herein, the term "superparamagnetic material" refers to material that exhibits a behavior similar to paramagnetism even when the temperature is below the Curie or the Néel temperature.

One aspect of the invention relates to a composition comprising a nanoparticle. The nanoparticle comprises a nanoparticulate transition metal oxide covalently functionalized with a silane-functionalized non-targeting zwitterionic moiety.

In some embodiments, the composition comprises the nanoparticle and other components, wherein the other components do not materially affect certain basic characteristics of the composition. In some embodiments, the other components do not materially affect the imaging, toxicity and clearance properties of the composition. Examples of such components include a buffer (such as sodium phosphate, for instance), an excipient (such as salts, disintegrators, binders, fillers, or lubricants, for instance), and a pharmaceutically acceptable carrier (such as water, for instance).

In some embodiments, the composition comprises a nanoparticle having an idealized structure I Structure I

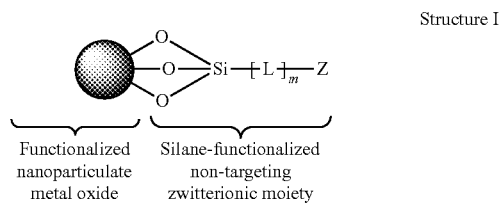

Functionalized nanoparticulate metal oxide | Silane-functionalized non-targeting zwitterionic moiety wherein, L is a linker, Z is the non-targeting zwitterionic moiety and m≥1. In structure I the nanoparticle composition is schematically shown as a spherical body representing the nanoparticulate metal oxide bound to a single silane functionalized non-targeting zwitterionic moiety. In addition, the nanoparticulate transition metal oxide can bound to two or more silane functionalized non-targeting zwitterionic moieties. The "idealized structure" as used herein refers to a schematic representation of an idealized form and may also include the structures wherein at least one of the oxygen atoms of the silane functionalized non-targeting zwitterionic moiety is covalently bound to the surface of nanoparticulate transition metal oxide. Those skilled in the art will recognize that methods for depositing species idealized in Structure V onto transition metal oxide nanoparticulate surfaces may also result in structures comprising Si—O—Si linkages which do not prevent the covalent bonding of the silanes to the nanoparticulate surface through alternative Si—O groups. In some embodiments, the "idealized structure" may also include the composition comprises silicon functionalized non targeting zwitterionic moieties that are covalently bound to the nanoparticulate surface solely through intermediate Si—O—Si linkages.

In some embodiments the nanoparticle represents a core-shell structure as described in FIG. 1. In FIG. 1, the nanoparticle 10 composition comprises a core 20, having a core surface 30. The core 20 represents the functionalized nanoparticulate transition metal oxide and the core surface 30 represents the surface of functionalized nanoparticulate transition metal oxide. The nanoparticle 10 further includes a shell 40, attached to the core surface 30. The shell 40 represents at least one silane-functionalized non-targeting zwitterionic moiety. The shell 40 is attached to the core surface 30 directly without any intervening layer, i.e. at least one silane functionalized non-targeting zwitterionic moiety is covalently bound via one or more oxygen-silicon bonds to the nanoparticulate metal oxide.

In some embodiment, the nanoparticulate transition metal oxide is selected from a group consisting of tungsten oxide, tantalum oxide, hafnium oxide, zirconium oxide, molybdenum oxide, bismuth oxide, silver oxide, zinc oxide, iron oxide, manganese oxide, copper oxide, cobalt oxide, nickel oxide, and combinations thereof.

In some embodiments, the nanoparticulate transition metal oxide comprises a single transition metal oxide such as tantalum oxide or iron oxide. In another embodiment, the nanoparticulate transition metal oxide comprises two or more transition metal oxides for example, tantalum oxide and hafnium oxide or iron oxide and manganese oxide.

In some embodiments, the nanoparticulate transition metal oxide may be substantially radiopaque, meaning that the nanoparticulate transition metal oxide substantially prohibits X-ray radiation to pass through the materials typically found in living organisms, thus potentially giving the particles utility as contrast agents in X-ray imaging applications, such as computed tomography (CT). Examples of transition metal oxides that may provide this property include but are not limited to tungsten oxide, tantalum oxide, hafnium oxide, zirconium oxide, molybdenum oxide, bismuth oxide, silver oxide, and zinc oxide. In one or more embodiments, the nanoparticulate transition metal oxide is tantalum oxide and the nanoparticle has an average particle size up to about 10 nm. These nanoparticles may be used for applications in imaging techniques that apply X-rays to generate imaging data, due to the high degree of radiopacity. Moreover the smaller size aids in rapid renal clearance.

In another embodiment, the nanoparticulate transition metal oxide exhibits magnetic behavior, including, for example, superparamagnetic behavior. Examples of potential magnetic or superparamagnetic nanoparticulate transition metal oxides include iron oxide, manganese oxide, copper oxide, cobalt oxide, or nickel oxide. In one embodiment, the superparamagnetic nanoparticulate transition metal oxide comprises superparamagnetic iron oxide. In some embodiments, the nanoparticles of the present invention may be used as magnetic resonance (MR) contrast agents. These nanoparticles may yield a T2*, T2, or T1 magnetic resonance signal upon exposure to a magnetic field. In one or more embodiments, the nanoparticulate transition metal oxide is superparamagnetic iron oxide and the nanoparticle has a particle size up to about 50 nm.

The silane functionalized non-targeting zwitterionic moiety comprises a silane moiety and a non-targeting zwitterionic moiety. The non-targeting zwitterionic moiety is connected to the silicon atom of the silane moiety via a linker. The silane-functionalized non-targeting zwitterionic moiety is covalently attached to the surface of the nanoparticulate transition metal oxide through one or more silicon oxygen bonds.

In some embodiments, two or more silane-functionalized non-targeting zwitterionic moieties are attached to the surface of the nanoparticulate transition metal oxide to substantially cover the nanoparticulate transition metal oxide. As used herein, the term "substantially cover" refers to a percentage surface coverage of the nanoparticulate transition metal oxide of greater than about 20%. Percentage surface coverage refers to the ratio of nanoparticulate metal oxide surface covered by the silane functionalized non-targeting zwitterionic moieties to the surface area not covered by the silane functionalized non-targeting zwitterionic moieties. In some embodiments, the percentage surface coverage of the nanoparticulate metal oxide may be greater than about 40%.

In some embodiments, two or more silane-functionalized non-targeting zwitterionic moieties attached to the surface of a nanoparticulate transition metal oxide may have the same or different chemical structures. In one embodiment, the nanoparticulate transition metal oxide is attached to two or more silane-functionalized non-targeting zwitterionic moieties, wherein each of the silane-functionalized non-targeting zwitterionic moieties has the same chemical structure. In another embodiment, the nanoparticulate transition metal oxide is attached to two or more non-targeting silane-functionalized zwitterionic moieties, wherein the silane-functionalized non-targeting zwitterionic moieties have different chemical structures.

The non-targeting zwitterionic moieties are non-fouling in nature in the presence of biological entities such as proteins during in-vivo administration. Therefore, these moieties prevent any substantial specific interaction between the functionalized nanoparticulate and biological entities found in the blood stream upon injection, which in turn leads to greater biocompatibility, lower toxicity and reduced chance for unintended species or tissue targeting.

The silane-functionalized non-targeting zwitterionic moieties may serve to stabilize the nanoparticulate transition metal oxide, i.e. the silane-functionalized non-targeting zwitterionic moieties may prevent one nanoparticulate transition metal oxide from contacting an adjacent nanoparticulate transition metal oxide, thereby preventing a plurality of such nanoparticle from aggregating, or by preventing leaching of metal or metal oxide.

In some embodiments, the silane functionalized non-targeting zwitterionic moieties may facilitate improved water solubility, reduce aggregate formation, reduce agglomerate formation, prevent oxidation of nanoparticles, maintain the uniformity of the core-shell structure, or provide biocompatibility for the nanoparticles. In some embodiments, the non-targeting zwitterionic moiety of the silane functionalized zwitterionic moiety may facilitate renal clearance of the nanoparticle composition from the body without causing short term or long term toxicity to one or more organs.

In some embodiments, the nanoparticle further includes silane-functionalized non-zwitterionic moieties, wherein the silane functionalized non-zwitterionic moieties are covalently attached to the surface of the nanoparticulate transition metal oxide. In such embodiments, a ratio of silane-functionalized non-targeting zwitterionic moieties to silane-functionalized non-zwitterionic moieties is from about 0.01 to about 200. In some other embodiments, the ratio of silane-functionalized non-targeting zwitterionic moieties to silane-functionalized non-zwitterionic moieties is from about 0.1 to about 20.

In another embodiment, the silane functionalized non-zwitterionic moiety may further comprise other materials that are tailored for a particular application, such as, but not limited to, diagnostic applications. For instance the silane functionalized non-zwitterionic moiety may further be functionalized with a targeting ligand, wherein the targeting ligand is attached to the silane functionalized non-zwitterionic moiety. The targeting ligand may be a molecule or a structure that provides targeting of the nanoparticle to a specific organ, tissue or cell. The targeting ligand may include, but is not limited to, proteins, peptides, antibodies, nucleic acids, sugar derivatives, or combinations thereof.

In some embodiments, the nanoparticle composition is a non-targeting contrast agent. In other embodiments, the nanoparticle composition is a targeting contrast agent, wherein a targeting ligand is attached to the silane-functionalized non-zwitterionic moieties.

In some embodiments, the silane functionalized non-zwitterionic moiety may be further functionalized with other polymers, wherein the polymers are attached to the silane functionalized non-zwitterionic moiety. The polymer may be water soluble and biocompatible. In one embodiment, the polymers include, but are not limited to, polyethylene glycol (PEG), polyethylene imine (PEI), polymethacrylate, polyvinylsulfate, polyvinylpyrrolidinone, or combinations thereof.

In some embodiments, the non-targeting zwitterionic moiety comprises a positively charged moiety, a negatively charged moiety and a spacer group in between the positively charged moiety and the negatively charged moiety. The positively charged moiety may originate from organic bases and the negatively charged moiety may originate from organic acids. FIG. 2 presents a list of exemplary organic acids and bases from which the negatively charged moiety and the positively charged moiety may originate.

In some embodiments, the positively charged moiety comprises protonated primary amines, protonated secondary amines, protonated tertiary alkyl amines, protonated amidines, protonated guanidines, protonated pyridines, protonated pyrimidines, protonated pyrazines, protonated purines, protonated imidazoles, protonated pyrroles, quaternary alkyl amines, or combinations thereof.

In some embodiments, the negatively charged moiety comprises deprotonated carboxylic acids, deprotonated sulfonic acids, deprotonated sulfinic acids, deprotonated phosphonic acids, deprotonated phosphoric acids, deprotonated phosphinic acids, or combinations thereof.

In one or more embodiments, the spacer group may be selected from a group consisting of alkyl groups, aryl groups, substituted alkyl and aryl groups, heteroalkyl groups, heteroaryl groups, carboxy groups, ethers, amides, esters, carbamates, ureas, straight chain alkyl groups of 1 to 10 carbon atoms in length, or combinations thereof. In one embodiment, the spacer group comprises less than 10 carbon atoms.

In some embodiments, the silane-functionalized zwitterionic moiety comprises the hydrolysis product of a precursor tri-alkoxy silane, such as those illustrated in FIG. 3A-3D. In some embodiments, the precursor tri-alkoxy silane comprises N,N-dimethyl-3-sulfo-N-(3-(trimethoxysilyl)propyl)propan-1-aminium, 3-(methyl(3-(trimethoxysilyl)propyl) amino)propane-1-sulfonic acid, 3-(3-(trimethoxysilyl)propylamino)propane-1-sulfonic acid, 2-(2-(trimethylsilyl) ethoxy(hydroxy)phosphoryloxy)-N,N,N-trimethylethanaminium, 2-(2-(trimethoxysilyl)ethyl (hydroxy)phosphoryloxy)-N,N,N-trimethylethanaminium, N,N,N-trimethyl-3-(N-3-(trimethoxysilyl)propionylsulfamoyl)propan-1-aminium, N-((2H-tetrazol-5-yl)methyl)-N,N-dimethyl-3-(trimethoxysilyl)propan-1-aminium, N-(2-carboxyethyl)-N,N-dimethyl-3-(trimethoxysilyl)propan-1-aminium, 3-(methyl(3-(trimethoxysilyl)propyl)amino) propanoic acid, 3-(3-(trimethoxysilyl)propylamino) propanoic acid, N-(carboxymethyl)-N,N-dimethyl-3-(trimethoxysilyl)propan-1-aminium, 2-(methyl(3-(trimethoxysilyl)propyl)amino)acetic acid, 2-(3-(trimethoxysilyl)propylamino)acetic acid, 2-(4-(3-(trimethoxysilyl)propylcarbamoyl)piperazin-1-yl)acetic acid, 3-(4-(3-(trimethoxysilyl)propylcarbamoyl)piperazin-1-yl)propanoic acid, 2-(methyl(2-(3-(trimethoxysilyl)propylureido)ethyl)amino)acetic acid, 2-(2-(3-(trimethoxysilyl) propylureido)ethyl)aminoacetic acid, or combinations thereof.

In one or more embodiments, the linker may be selected from a group consisting of alkyl groups, aryl groups, substituted alkyl and aryl groups, heteroalkyl groups, heteroaryl groups, carboxy groups, ethers, amides, esters, carbamates, ureas, straight chain alkyl groups of 1 to 10 carbon atoms in length, or combinations thereof. In one embodiment, the linker group comprises less than 10 carbon atoms.

In some embodiments, a composition comprises a nanoparticle. The nanoparticle comprising a nanoparticulate tantalum oxide covalently functionalized with N,N-dimethyl-3- sulpho-N-(3-(trimethoxysilyl)propyl)propane-1-aminium. In one of the embodiments, the nanoparticle has an idealized structure II;

Structure II

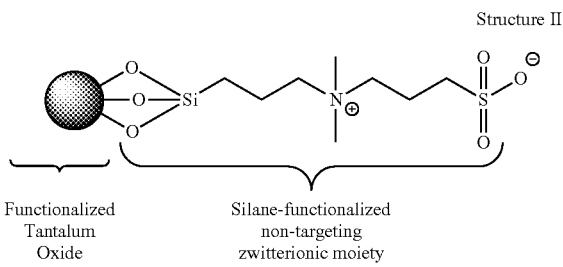 [SMILES: CO[Si](CCC[N+](C)(C)CCCS(=O)(=O)[O-])(OC)OC]

Functionalized Tantalum Oxide

Silane-functionalized non-targeting zwitterionic moiety

In some embodiments, the composition comprises a nanoparticle. The nanoparticle comprises a nanoparticulate tantalum oxide covalently functionalized with 2-(4-(3-(trimethoxysilyl)propylcarbamoyl)piperazine-1-yl)acetic acid. In one of the embodiments, the nanoparticle has an idealized structure III;

Structure III

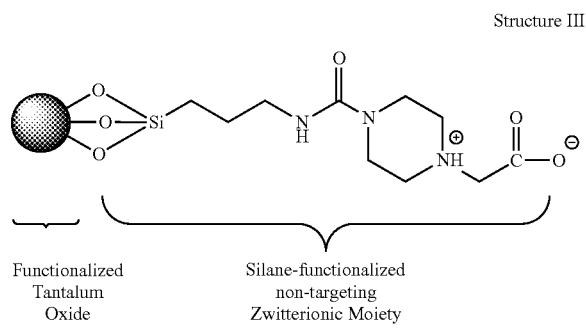 [SMILES: CO[Si](CCCNC(=O)N1CC[NH+](CC(=O)[O-])CC1)(OC)OC]

Functionalized Tantalum Oxide

Silane-functionalized non-targeting Zwitterionic Moiety

In some embodiments, the composition comprises a nanoparticle. The nanoparticle comprises a nanoparticulate tantalum oxide covalently functionalized with a trioxysilane betaine ligand. In one embodiment, the nanoparticle has an idealized structure IV;

Structure IV

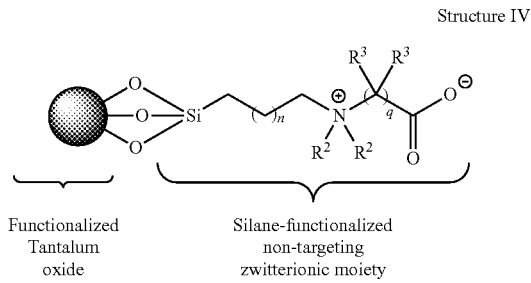

Functionalized Tantalum oxide

Silane-functionalized non-targeting zwitterionic moiety wherein $R^2$ is independently at each occurrence a $C_1$-$C_3$ alkyl group; $R^3$ is independently at each occurrence a hydrogen or a $C_1$-$C_3$ alkyl group; n is 0, 1, 2 or 3; q is 1, 2 or 3.

In some embodiments a composition comprising a nanoparticle of the present invention is described. In some embodiments, the composition comprises a plurality of such nanoparticles. The plurality of nanoparticles may be either of same chemical composition or of different chemical compositions. The plurality of nanoparticles may be characterized by one or more median particle size, average diameter or particle size, particle size distribution, average particle surface area, particle shape, or particle cross-sectional geometry. Furthermore, a plurality of nanoparticles may have a distribution of particle sizes that may be characterized by both a number-average size and a weight-average particle size. The number-average particle size may be represented by $S_N = \Sigma (s_i n_i)/\Sigma n_i$, where $n_i$ is the number of particles having a particle size $s_i$. The weight average particle size may be represented by $S_W = \Sigma(s_i n_i^2)/\Sigma(s_i n_i)$. When all particles have the same size, $S_N$ and $S_W$ may be equal. In one embodiment, there may be a distribution of sizes, and $S_N$ may be different from $S_W$. The ratio of the weight average to the number average may be defined as the polydispersity index ($S_{PDI}$). In one embodiment, $S_{PDI}$ may be equal to about 1. In other embodiments, respectively, $S_{PDI}$ may be in a range of from about 1 to about 1.2, from about 1.2 to about 1.4, from about 1.4 to about 1.6, or from about 1.6 to about 2.0. In one embodiment, $S_{PDI}$ may be in a range that is greater than about 2.0.

In one embodiment, the plurality of nanoparticles may have a particle size distribution selected from a group consisting of normal distribution, monomodal distribution, and bimodal distribution. Certain particle size distributions may be useful to provide certain benefits. A monomodal distribution may refer to a population of particles having one distinct sub-population size range. In another embodiment, populations of particles having two distinct sub-population size ranges (a bimodal distribution) may be included in the composition.

In one embodiment, the plurality of nanoparticles may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, or a cube. In one embodiment, a cross-sectional geometry of the particle may be one or more of circular, ellipsoidal, triangular, rectangular, or polygonal. In one embodiment, a nanoparticle may consist essentially of non-spherical particles. For example, such particles may have the form of ellipsoids, which may have all three principal axes of differing lengths, or may be oblate or prelate ellipsoids of revolution. Non-spherical nanoparticles alternatively may be laminar in form, wherein laminar refers to particles in which the maximum dimension along one axis is substantially less than the maximum dimension along each of the other two axes. Non-spherical nanoparticles may also have the shape of frusta of pyramids or cones, or of elongated rods. In one embodiment, the nanoparticles may be irregular in shape. In one embodiment, a plurality of nanoparticles may consist essentially of spherical nanoparticles. In one embodiment, the nanoparticle may have a high surface-to-volume ratio.

In one embodiment, the plurality of nanoparticles may comprise a single type (size, shape, and the like) of nanoparticle, or mixtures of different types of nanoparticles. If a mixture of nanoparticles is used they may be homogeneously or non-homogeneously distributed in the composition.

In one embodiment, the nanoparticle may be stable towards aggregate or agglomerate formation. An aggregate may include more than one nanoparticle in physical contact with one another, while agglomerates may include more than one aggregate in physical contact with one another. In some embodiments, the nanoparticles may not be strongly agglomerated and/or aggregated such that the particles may be relatively easily dispersed in the composition. In one embodiment, the plurality of nanoparticles may have a median particle size up to about 50 nm. In another embodiment, the plurality of nanoparticles may have a median particle size up to about 10 nm. In another embodiment, the plurality of nanoparticles may have a median particle size up to about 6 nm. A small particle size may be advantageous in facilitating clearance from kidneys and other organs.

Another aspect of the invention relates to a diagnostic agent composition. The diagnostic agent composition comprises a plurality of the nanoparticles as described previously. In one embodiment, the diagnostic agent composition further comprises a pharmaceutically acceptable carrier and optionally one or more excipients. In one embodiment, the pharmaceutically acceptable carrier may be substantially water. Optional excipients may comprise one or more of salts, disintegrators, binders, fillers, or lubricants.

One aspect of the invention relates to methods for making a nanoparticle. The method comprises (a) providing a nanoparticulate transition metal oxide and (b) reacting a silane-functionalized non-targeting zwitterionic moiety with the nanoparticulate transition metal oxide; wherein the silane-functionalized non-targeting zwitterionic moiety has structure V as described above. It will be understood that the order and/or combination of steps may be varied. Thus, according to some embodiments, steps (a) and (b) occur as sequential steps so as to form the nanoparticle.

In one or more embodiments, the step of providing a nanoparticulate transition metal oxide comprises providing a first precursor material, wherein the first precursor material comprises at least one transition metal. In one embodiment, the first precursor material may react to generate the nanoparticulate transition metal oxide. In one embodiment, the first precursor material may decompose to generate the nanoparticulate transition metal oxide. In another embodiment, the first precursor material may hydrolyze to generate the nanoparticulate transition metal oxide. Nanoparticle synthesis methods are well known in the art and any suitable method for making a nanoparticulate transition metal oxide of an appropriate material may be suitable for use in this method.

In some embodiments, the first precursor material comprises at least one transition metal; and step (a) further comprises hydrolysis of the first precursor material. According to some embodiments, the first precursor material is an alkoxide or halide of the transition metal, and the hydrolysis process includes combining the first precursor material with an acid and water in an alcoholic solvent. In one embodiment, the metal alkoxide may be a tantalum alkoxide such as tantalum ethoxide, the organic acid may be a carboxylic acid such as isobutyric acid, propionic acid or acetic acid and the hydrolysis reaction may be carried out in the presence of an alcohol solvent such as 1-propanol or methanol.

In one or more embodiments, the step of reacting a silane-functionalized non-targeting zwitterionic moiety with the nanoparticulate transition metal oxide comprises providing a second precursor material, such as a material comprising a silane moiety or a precursor to a silane moiety. In one embodiment the silane moiety reacts with the nanoparticulate transition metal oxide. In another embodiment, the precursor undergoes a hydrolysis reaction before reacting with the nanoparticulate transition metal oxide. In some embodiments, the silane moiety is functionalized with at least one non-targeting zwitterionic moiety or at least one precursor to a non-targeting zwitterionic moiety. In embodiments wherein the silane moiety is functionalized with at least one non-targeting zwitterionic moiety, a silane-functionalized zwitterionic moiety reacts with the nanoparticulate transition metal oxide. In embodiments wherein the silane moiety is functionalized with a precursor to a non-targeting zwitterionic moiety, first a silane moiety reacts with the nanoparticulate transition metal oxide. The silane moiety may not be zwitterionic in nature, but subsequently reacts with an appropriate reagent to convert the precursor into a non-targeting zwitterionic moiety. In one or more embodiments, the second precursor material comprises the silane-functionalized non-targeting zwitterionic moiety or precursor to a silane-functionalized non-targeting zwitterionic moiety, such as one or more of the precursor tri-alkoxy silanes described above. At least one of the organofunctional tri-alkoxy silanes contains at least one non-targeting zwitterionic group or a precursor to a non-targeting zwitterionic group.

In other embodiments, the nanoparticulate transition metal oxide is treated with a mixture containing at least two silane moieties. In one embodiment, one silane moiety is functionalized with a non-targeting zwitterionic moiety, or a precursor to a non-targeting zwitterionic moiety and the second silane moiety may not be functionalized with any zwitterionic moiety. The silane moieties may be added either simultaneously or sequentially.

In one embodiment, a nanoparticulate tantalum oxide may be allowed to react with an alkoxy silane that contains both a quaternary nitrogen as well as a sulfonate group or a carboxy group, for example, a sulfobetaine group or a betaine group. In one embodiment the nanoparticulate tantalum oxide may be allowed to react with $(RO)_3Si(CH_2)_xNR'_2(CH_2)_ySO_3$, where R is an alkyl or aryl group, x is 1-10, y is 1-10, and R' is H, an alkyl group or an aryl group. In one embodiment, the R is an alkyl group, such as methyl or ethyl, x is 3, y is between 2-5, and R' is H or an alkyl group such as methyl.

In one embodiment, sulfobetaine-functionalized silanes may be synthesised upon the ring opening reaction of alkyl sultones or a mixture of alkyl sultones with amine substituted silanes. In another embodiment, alkyl lactones or mixtures of alkyl lactones may be used in place of the alkyl sultones. In certain embodiments, the silane functionalized zwitterionic moiety comprises a mixture of sulfobetaine and betaine functional silanes. In another embodiment, the nanoparticulate transition metal oxide may react with a sulfobetaine or betaine functional silane moiety, in which the sulfonate or carboxy group may be chemically protected.

In another embodiment, the nanoparticulate tantalum oxide may be allowed to react with an amine-containing silane, such as an amino-functional trialkoxysilane, to form a nanoparticulate tantalum oxide functionalized with the amine-containing silane. In a second step, the nanoparticulate tantalum oxide functionalized with the silane may be isolated. In an alternative embodiment, the nanoparticulate tantalum oxide functionalized with the silane may be used in-situ. The nanoparticulate tantalum oxide functionalized with the silane may be allowed to react with an alkyl sultone, an alkyl lactone, a haloalkylcarboxylic acid or ester, mixtures of alkyl sultones, mixtures of alkyl lactones, mixtures of haloalkylcarboxylic acids or esters, or mixtures of both alkyl sultones and alkyl lactones to form a non-targeting zwitterionic moiety. The amount of sultone, lactone or mixture of sultones and/or lactones may be sufficient to provide, on average, at least one non-targeting zwitterionic moiety per nanoparticle. Non-limiting examples of alkyl sultones include propane sultone and butyl sultone. Non-limiting examples of lactones include propane lactone and butyl lactone.

In one embodiment, the method further comprises fractionating the plurality of nanoparticles. The fractionating step may include filtering the nanoparticles. In another embodiment, the method may further comprise purifying the plurality of nanoparticles. The purification step may include use of dialysis, tangential flow filtration, diafiltration, or combinations thereof. In another embodiment, the method further comprises isolation of the purified nanoparticles.

In combination with any of the above-described embodiments, some embodiments relate to a method for making a diagnostic agent composition for X-ray/computed tomography or MRI. The diagnostic agent composition comprises a plurality of nanoparticles. In some embodiments, the median particle size of the plurality of nanoparticles may not be more than about 10 nm. It will be understood that according to some embodiments, the particle size of the plurality of nanoparticles may be selected so as to render the nanoparticle substantially clearable by a mammalian kidney, such as a human kidney, in particulate form.

In some embodiments, the present invention is directed to a method of use of the diagnostic agent composition comprising a plurality of the nanoparticles described herein. In some embodiments, the method comprises the in-vivo or in-vitro administration of the diagnostic agent composition to a subject, which in some instances may be a live subject, such as a mammal, and subsequent image generation of the subject with an X-ray/CT device. The nanoparticles, as described above, comprise a nanoparticulate transition metal oxide and a silane functionalized non-targeting zwitterionic moiety as described in structure I. In one embodiment, the nanoparticulate transition metal oxide is tantalum oxide. The nanoparticle may be introduced to the subject by a variety of known methods. Non-limiting examples for introducing the nanoparticle to the subject include intravenous, intra-arterial or oral administration, dermal application, or direct injection into muscle, skin, the peritoneal cavity or other tissues or bodily compartments.

In another embodiment, the method comprises administering the diagnostic agent composition to a subject, and imaging the subject with a diagnostic device. The diagnostic device employs imaging methods, examples of which include, but are not limited to, MRI, optical imaging, optical coherence tomography, X-ray, computed tomography, positron emission tomography, or combinations thereof. The diagnostic agent composition, as described above, comprises a plurality of the nanoparticles.

In one embodiment, the methods described above for use of the diagnostic contrast agent further comprise monitoring delivery of the diagnostic agent composition to the subject with the diagnostic device, and diagnosing the subject; in this method data may be compiled and analyzed generally in keeping with common operation of medical diagnostic imaging equipment. The diagnostic agent composition may be an X-ray or CT contrast agent, for example, such as a nanoparticles having nanoparticulate tantalum oxide. The diagnosing agent composition may provide for a CT signal in a range from about 100 Hounsfield to about 5000 Hounsfield units. In another example, the diagnostic agent composition may be a MRI contrast agent, such as an agent comprising a superparamagnetic iron oxide.

One embodiment of the invention provides a method for determination of the extent to which the nanoparticles described herein, such as nanoparticles having nanoparticulate tantalum oxide or iron oxide, are distributed within a subject. The subject may be a mammal or a biological material comprising a tissue sample or a cell. The method may be an in-vivo or in-vitro method. The nanoparticle may be introduced to the subject by a variety of known methods. Non-limiting examples for introducing the nanoparticle to the subject include any of the known methods described above. In one embodiment, the method comprises (a) introducing the nanoparticles into the subject, and (b) determining the distribution of the nanoparticles in the subject. Distribution within a subject may be determined using a diagnostic imaging technique such as those mentioned previously. Alternatively, the distribution of the nanoparticle in the biological material may be determined by elemental analysis. In one embodiment, Inductively Coupled Plasma Mass Spectroscopy (ICP-MS) may be used to determine the concentration of the nanoparticle in the biological material.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLES

Practice of the invention will be still more fully understood from the following examples, which are presented herein for illustration only and should not be construed as limiting the invention in any way.

The abbreviations used in the examples section are expanded as follows: "mg": milligrams; "mL": milliliters; "mg/mL": milligrams per milliliter; "mmol": millimoles; "µL" and µLs: microliters "LC": Liquid Chromatography; "DLS": Dynamic Light Scattering; "DI": Deionized water, "ICP": Inductively Coupled Plasma.

Unless otherwise noted, all reagent-grade chemicals were used as received, and Millipore water was used in the preparation of all aqueous solutions.

Synthesis of Tantalum Oxide-Based Nanoparticles

Step-1: Synthesis of N,N-dimethyl-3-sulfo-N-(3-(trimethoxysilyl)propyl)propan-1-aminium Toluene (anhydrous, 250 mL), N,N-dimethylaminotrimethoxysilane (25 g, 121 mmol) and 1,3-propane sultone (13.4 g, 110 mmol) were added to a 500 mL round bottom flask containing a stir bar. The mixture was stirred at room temperature for 4 days. The mixture was then filtered to isolate the precipitated product, which was subsequently washed with fresh anhydrous toluene (2×60 mL). The yield of white powder after drying under vacuum was 23.6 g.

Step-2: Reaction of N,N-dimethyl-3-sulfo-N-(3-(trimethoxysilyl)propyl)propan-1-aminium with nanoparticulate Tantalum oxide Method-1: 1-Propanol as Solvent A 250 mL three necked round bottomed flask containing a stir bar was charged with 1-propanol (73 mL), followed by addition of isobutyric acid (1.16 mL, 12.51 mmol, 1.27 eq with respect to Ta) and DI water (1.08 mL, 59.95 mmol, 6.09 eq with respect to Ta) to form a reaction mixture. Nitrogen was bubbled through the reaction mixture for 20 minutes followed by dropwise addition of tantalum ethoxide $(Ta(OEt)_5)$ (2.55 mL, 4 g, 9.84 mmol) to the reaction mixture at room temperature with stirring over 15 minutes. During the addition of $Ta(OEt)_5$, the nitrogen was caused to continue to bubble through the reaction mixture. The above mentioned reaction mixture was allowed to stir at room temperature under nitrogen for 16 hours after the $Ta(OEt)_5$ addition was complete.

The reaction mixture was stirred at room temperature for 16 hours and then an aliquot (1.5 mL) was taken out from the reaction mixture, filtered through a 20 nm filtration membrane, and the particle size was measured (as the hydrodynamic radius) in water by DLS immediately after the filtration step. The average particle size was measured to be approximately 3.6 nm. N,N-dimethyl-3-sulfo-N-(3-(trimethoxysilyl)propyl)propan-1-aminium (4.03 g, 12.23 mmol, 1.24 eq with respect to Ta) was dissolved in 50 mL of DI water. This solution was added to the above mentioned reaction mixture dropwise over a few minutes. The colorless, homogeneous reaction mixture was changed immediately into a cloudy white solution and finally became a milky solution by the end of the addition of the silane-functionalized zwitterionic moiety. After the addition was complete a condenser was attached to the flask, and the reaction mixture was kept under a nitrogen blanket. The flask was placed in an oil bath preheated to 75° C. and the reaction mixture was stirred for 6 hours. The reaction mixture became clearer. After 6 hours, the reaction mixture was cooled to room temperature under a blanket of air. The heterogeneous reaction mixture was neutralized to pH 6-7 using 1M $NH_4OH$. The reaction mixture was transferred into a second round bottom flask under a blanket of air. During the transfer of the reaction mixture to the second flask, an amount of white material remained in the flask, and did not get transferred to the second flask (crude product A). This crude product A was dried under a flow of nitrogen overnight. Meanwhile, the solution of the second flask was evaporated using a rotary evaporator at 50° C. The dry white residue obtained after the evaporation of the solution, (crude product B) was allowed to stand under a nitrogen flow over night.

The crude product A was dried overnight. This solid was completely dissolved in DI water. Crude product B was also completely dissolved in DI water, and the two solutions (crude product A & crude product B) were combined (total volume was 60 mL). The aqueous solution was filtered sequentially through 450 nm, 200 nm and 100 nm filtration membranes and finally through a 20 nm filtration membrane. The solution was then first dialyzed at pH 7.0 using sodium phosphate buffer (10K molecular weight cut-off snakeskin regenerated cellulose tubing), and then three times in DI water.

Finally, the nanoparticle was isolated by lyophilization. Yield of white powder=1.748 g (38% yield based on Ta). Zeta potential: (−)8.18 mV. Elemental analysis: 38.3±0.3% Ta, 4.8±0.1% Si. The average particle size was measured to be 8.9 nm by DLS. Purity of the nanoparticle was measured by Liquid Chromatography (LC)/Inductively Coupled Plasma (ICP).

Method-2: Trifluoroethanol as Solvent

A 100 mL three necked round bottom flask containing a stir bar was charged with trifluoroethanol (42 mL). While the solvent was sparged with nitrogen, isobutyric acid (0.53 mL, 5.7 mmol) followed by water (0.13 mL, 7.4 mmol) were added using a syringe. The solution was allowed to stir for an additional 15 min with continuous nitrogen bubbling. Tantalum ethoxide $(Ta(OEt)_5)$ (2 g, 4.9 mmol) was added dropwise using a syringe. The slightly hazy solution was allowed to stir at room temperature under nitrogen for 17 hours. N,N-dimethyl-3-sulfo-N-(3-(trimethoxysilyl)propyl)propan-1-aminium (3.2 g, 9.8 mmol) was dissolved in water (15 mL). This homogeneous, colorless solution was added to the tantalum containing reaction mixture dropwise but quickly under air with stirring. The flask was fitted with a condenser and then placed in an oil bath preheated to 78° C. After stirring at this temperature for 6 hours, the colorless, homogeneous reaction mixture was cooled to room temperature. Trifluoroethanol was substantially removed in a rotary evaporator after adding water (20 mL). The aqueous solution was neutralized using concentrated ammonium hydroxide and then filtered successively through 200 nm, 100 nm and then 20 nm filters. The solution was then dialyzed using 3500 MW cut-off regenerated cellulose snake skin dialysis tubing 4 times. The first dialysis was performed in 50:50 DI water to pH 7.0 phosphate buffer. Subsequent dialyses were performed in DI water. The purified nanoparticle product was not isolated from water. A percent solids test on an aliquot was used to determine that the yield of coated nanoparticles was 1.55 g. The average particle size was determined by dynamic light scattering to be 1.6 nm.

Synthesis of Tantalum Oxide-Based Nanoparticle

Step-1: Synthesis of Ethyl 2(4(3(trimethoxysilyl)propylcarbamoyl)piperazin-1-yl)acetate (3-isocyanatopropyl)trimethoxysilane (4.106 g) was added to a solution of ethylacetoxypiperazine (3.789 g) in methylene chloride (20 mL). The solution was stirred for 16 hours, and then the solvent was removed under reduced pressure, yielding 8.37 g of material that was used without further purification.

Step-2: Reaction of Ethyl 2-(4-(3-(trimethoxysilyl)propylcarbamoyl)piperazin-1-yl)acetate with nanoparticulate tantalum oxide A 500 mL round-bottom flask was charged with n-propanol (99 mL), isobutyric acid (1.4 mL), and water (1.2 mL). The solution was stirred for 5 min, then $Ta(OEt)_5$ (5.37 g) was added dropwise to the solution. The solution was stirred at room temperature under nitrogen for 18 hours. A total of 60 mL of this solution was then added to ethyl 2-(4-(3-(trimethoxysilyl)propylcarbamoyl)piperazin-1-yl)acetate (6.37 g), and the solution was stirred under nitrogen for 2 hours at 100° C. The mixture was then cooled to room temperature, water (20 mL) was added, and the mixture was stirred for 18 hours at room temperature. A total of 75 mL of 0.33 N aqueous hydrochloric acid was then added, and the solution was heated to 60° C. for 6 hours. The mixture was then cooled to room temperature, 250 mL of 28% aqueous ammonia was added, and the mixture was stirred for 5 days. The ammonia and propanol were removed under reduced pressure, then the material was poured into 3,000 MW cut-off regenerated cellulose dialysis tubing, and dialyzed against distilled water for 48 hours, changing the dialysis buffer every 12 hours. The solution was then filtered through 30,000 MW cut-off centrifuge filters, yielding particles with an average size of 4.5 nm, as measured by DLS.

Synthesis of Iron Oxide-Based Nanoparticle

Synthesis of Nanoparticulate Superparamagnetic Iron Oxide

A 100 mL three-necked round bottom flask was charged with 706 mg of $Fe(acac)_3$ and 20 mL of anhydrous benzyl alcohol. The solution was sparged with nitrogen and then heated to 165° C. for 2 hours under a nitrogen atmosphere. The solution was then cooled to, and stored, at room temperature.

Reaction of Ethyl 2-(4-(3-(trimethoxysilyl)propyl-carbamoyl)piperazin-1-yl)acetate with superparamagnetic iron oxide A 10 mL aliquot of superparamagnetic iron oxide nanoparticles in benzyl alcohol (5.58 mg Fe/mL) was diluted with 50 mL of tetrahydrofuran. 2.00 g of ethyl 2-(4-(3-(trimethoxysilyl)propylcarbamoyl)piperazin-1-yl)acetate was added, and the mixture was heated to 60° C. with stirring for 2 hours, followed by cooling to room temperature. 50 mL of 1.0 M aqueous potassium carbonate was added after which the flask was then sealed and heated with stirring to 60° C. for 18 hours. The mixture was then cooled and centrifuged, and the aqueous layer was poured into 10,000 MW cut-off regenerated cellulose dialysis tubing and dialyzed vs 4 liters of 10 mM sodium citrate for 48 hours, changing the dialysis buffer every 12 hours. The final volume was 94 mL, with a total of 0.416 mg iron per mL of solution. The material had an average particle size of 8.4 nm in 150 mM aqueous sodium chloride as measured by dynamic light scattering.

Reaction of N,N-dimethyl-3-sulfo-N-(3-(trimethoxysilyl)propyl)propan-1-aminium with superparamagnetic iron oxide A 16.75 mL aliquot of superparamagnetic iron oxide nanoparticles in benzyl alcohol (5.58 mg Fe/mL) was added to tetrahydrofuran for a total volume of 94.5 mL. This solution was then added to a pressure flask, along with 3.1 g of N,N-dimethyl-3-sulfo-N-(3-(trimethoxysilyl)propyl)propan-1-aminium, and the mixture was heated to 50° C. with stirring for 2 hours. After cooling to room temperature, a total of 31 mL of isopropanol and 76 mL of concentrated aqueous ammonium hydroxide (28% $NH_3$ in water) were added; the flask was then sealed and heated to 50° C. with stirring for 18 hours. The mixture was cooled and washed with hexanes (100 mL×3). The aqueous layer was poured into 10,000 MW cut-off regenerated cellulose dialysis tubing, and dialyzed vs 4 liters of 10 mM sodium citrate for 18 hours. The final solution had a total of 0.67 mg iron per mL of solution. The material had a particle size of 9.2 nm.

Determination of the Particle Size and Stability of the Nanoparticles in Water

Nanoparticles from method 1 (36.2 mg) were dissolved in 2 mL of DI water. The solution was filtered through a 20 nm filtration membrane. The average particle size was measured as a hydrodynamic radius by dynamic light scattering (DLS), immediately after the filtration step. The sample was stored for 15 days at 37° C., with periodic monitoring by DLS. The results are shown in Table 1.

TABLE 1

| Time (t) | Average particle size* |
|---|---|
| 0 | 10.1 nm |
| 5 days | 12.8 nm |
| 15 days | 12.2 nm |

*Average particle size was measured at 37° C., using DLS.

Nanoparticle Biodistribution Studies

In-vivo studies were carried out with male Lewis rats with a size range between 150 and 500 grams body weight. Rats were housed in standard housing with food and water ad libitum and a 12 hour day-night lighting cycle. All animals used for biodistribution were otherwise untreated, normal subjects.

Nanoparticles were administered as a filter-sterilized solution in either water or saline. Administration was performed under isoflurane anesthesia (4% induction, 2% maintenance) via a 26 G catheter inserted into the lateral tail vein. Injection volumes were determined based on the concentration of the nanoparticles in the injectate and the size of the rat, but were generally less than 10% of rodent blood volume. The target dose was 100 mg of metal (e.g., tantalum) per kg of body weight. Once injected, animals were removed from anesthesia and, after a period of observation for adverse effects, returned to normal housing. At a later period of as short as a few minutes to as long as 6 months, the rats were euthanized, and organs of interest were harvested, weighed, and analyzed for their total metal (e.g., tantalum) content by ICP analysis. Along with the organs, a sample of the injected material was submitted to determine the exact concentration of injectate. These combined data determined the percentage of the injected dose ("% ID") remained in a tissue of interest. These data were reported either as % ID/organ, or % ID/gram of tissue. Experiments were generally performed with four duplicate rats at each time-point, allowing for the determination of experimental error (±standard deviation).

TABLE 2

| Coating | Kidney (% ID/organ) | Liver (% ID/organ) | Spleen (% ID/organ) |
|---|---|---|---|
| Diethylphosphatoethyl-triethoxysilane(PHS) | 4.2 ± 0.43 | 2.57 ± 0.64 | 0.16 ± 0.05 |
| N,N-dimethyl-3-sulfo-N-(3-(trimethoxy-silyl)propyl)propan-1-aminium (SZWIS) | 0.29 ± 0.05 | 0.24 ± 0.02 | ND |
| N-(2-carboxyethyl)-N,N-dimethyl-3-(trimethoxy-silyl)propan-1-aminium (CZWIS) | 0.70 ± 0.47 | 0.33 ± 0.03 | 0.04 ± 0.01 |

Table-2 describes the biodistribution of fractionated nanoparticles with non-zwitterionic (PHS) and zwitterionic coatings (SZWIS and CZWIS) in major clearing organs at 1 week following IV injection. "ND" stands for "not detected".

The amount of tantalum retained per organ is represented in the Table-2 as the fraction of the injected dose. Comparably sized non-zwitterionic coated nanoparticles are retained at much higher levels (almost one order of magnitude) than either of the zwitterionic coatings tested.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A composition comprising, a nanoparticle comprising a nanoparticulate transition metal oxide covalently functionalized with a silane-functionalized non-targeting zwitterionic moiety, wherein the nanoparticulate transition metal oxide is directly attached to the silane-functionalized non-targeting zwitterionic moiety without any intervening layer, and wherein the silane-functionalized non-targeting zwitterionic moiety comprises a reaction product of a precursor tri-alkoxy silane, wherein the precursor tri-alkoxy silane is selected from the group consisting of N-((2H-tetrazol-5-yl)methyl)-N,N-dimethyl-3-(trimethoxysilyl)propan-1-aminium, 2-(4-

(3-(trimethoxysilyl)propylcarbamoyl)piperazin-1-yl)acetic acid, 3-(4-(3-(trimethoxysilyl)propylcarbamoyl)piperazin-1-yl)propanoic acid, and combinations thereof.

2. The composition of claim 1, wherein the nanoparticle has a particle size up to about 50 nm.

3. The composition of claim 1, wherein the nanoparticle further comprises a silane-functionalized non-zwitterionic moiety.

4. The composition of claim 3, wherein a ratio of silane-functionalized non-targeting zwitterionic moieties to silane-functionalized non-zwitterionic moieties is from about 0.1 to about 20.

5. The composition of claim 3, wherein the nanoparticle further comprises a targeting ligand, wherein the targeting ligand is attached to the silane-functionalized non-zwitterionic moiety.

6. The composition of claim 1, further comprising a pharmaceutically acceptable carrier or excipient.

7. A composition comprising, a nanoparticle comprising a nanoparticulate tantalum oxide covalently functionalized with 2-(4-(3-(trimethoxysilyl)propylcarbamoyl)piperazine-1-yl)acetic acid.

8. The composition of claim 7, wherein the nanoparticle has a particle size up to about 10 nm.

9. The composition of claim 7, wherein the nanoparticle further comprises a silane-functionalized non-zwitterionic moiety.

10. The composition of claim 9, wherein the nanoparticle further comprises a targeting ligand, wherein the targeting ligand is attached to the silane-functionalized non-zwitterionic moiety.

11. The composition of claim 10, wherein a ratio of silane-functionalized non-targeting zwitterionic moieties to silane-functionalized non-zwitterionic moieties is from about 0.1 to about 20.

* * * * *